United States Patent
Racicot et al.

(12) 
(10) Patent No.: US 6,247,592 B1
(45) Date of Patent: *Jun. 19, 2001

(54) SYSTEM FOR DISPOSAL OF CONTAMINATED MEDICAL PRODUCTS

(75) Inventors: Douglas A. Racicot, Tolland; P. Spencer Kinsey, Newington; Richard G. Holdaway, Storrs; Gary L. Edmond, Canterbury; Gregory F. Biancardi, South Windsor, all of CT (US)

(73) Assignee: Bio-Plexus, Inc., Vernon, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/963,283

(22) Filed: Nov. 3, 1997

Related U.S. Application Data (63) Continuation of application No. 08/670,270, filed on Jun. 21, 1996, now abandoned.

(51) Int. Cl.[7] .................................................. A61M 5/32
(52) U.S. Cl. ........................................... 206/366; 220/908
(58) Field of Search .................................. 206/364, 366, 206/367, 368, 369, 370; 128/763; 220/908

(56) References Cited

U.S. PATENT DOCUMENTS

| | | |
|---|---|---|
| Re. 16,836 | 12/1927 | Cook . |
| D. 292,037 | 9/1987 | Hanifl . |
| D. 302,291 | 7/1989 | Heubel et al. . |
| D. 304,109 | 10/1989 | Hanifl . |
| D. 304,493 | 11/1989 | Bemis . |
| D. 306,509 | 3/1990 | Hanifl et al. . |
| D. 326,343 | 5/1992 | Hradisky . |
| D. 335,372 | 5/1993 | Mosior . |
| D. 335,373 | 5/1993 | Mosior . |

(List continued on next page.)

FOREIGN PATENT DOCUMENTS

| | | |
|---|---|---|
| 2112759 | 7/1994 | (CA) . |
| 883053 | 11/1952 | (DE) . |
| 802351 | 10/1958 | (DE) . |
| 2147183 | 4/1973 | (DE) . |
| 2740335 | 3/1979 | (DE) . |
| 3049503 | 7/1982 | (DE) . |
| 3903974 | 8/1990 | (DE) . |
| 0080882 | 6/1983 | (EP) . |
| 0304619 | 3/1989 | (EP) . |
| 2564726 | 11/1985 | (FR) . |
| 2040268 | 8/1980 | (GB) . |
| 2198644 | 6/1988 | (GB) . |
| 801838 | 2/1981 | (SU) . |
| 8905118 | 6/1989 | (WO) . |

OTHER PUBLICATIONS

U.S. application No. 08/904,811, Racicot et al., filed Aug. 1, 1997.

*Primary Examiner*—Jacob K. Ackun
(74) *Attorney, Agent, or Firm*—Libert & Associates (57) ABSTRACT

A disposed system for medical waste, and particularly sharp ended waste, includes a sharps receptacle and a companion needle holder. The needle holder has an actuation mechanism capable of detachably mounting an externally threaded hub of a needle assembly to the holder. The sharps receptacle has a top with an automatic release structure disposed thereon for engagement with the actuation mechanism of the needle holder. The automatic release structure cooperates with the actuation mechanism of the needle holder to automatically detach a mounted needle assembly from the holder into the sharps receptacle in response to placement of the holder into the automatic release structure.

36 Claims, 4 Drawing Sheets

U.S. PATENT DOCUMENTS

| | | |
|---|---|---|
| 357,421 | 2/1887 | Spencer . |
| 619,188 | 2/1899 | Kirkwood . |
| 1,088,962 | 3/1914 | Bostwick . |
| 1,231,497 | 6/1917 | Cook . |
| 1,667,454 | 4/1928 | Brix . |
| 1,757,680 | 5/1930 | Neil . |
| 2,376,436 | 5/1945 | Lawshe . |
| 2,392,196 | 1/1946 | Smith . |
| 2,672,866 | 3/1954 | Kater . |
| 3,159,159 | 12/1964 | Cohen . |
| 3,469,750 | 9/1969 | Vanderbeck . |
| 3,683,733 | 8/1972 | Johan et al. . |
| 3,706,306 | 12/1972 | Berger et al. . |
| 3,876,067 | 4/1975 | Schwarz . |
| 3,974,832 | 8/1976 | Kruck . |
| 4,150,666 | 4/1979 | Brush . |
| 4,154,229 | 5/1979 | Nugent . |
| 4,155,350 | 5/1979 | Percarpio . |
| 4,333,478 | 6/1982 | Krieg . |
| 4,351,434 | 9/1982 | Elisha . |
| 4,375,849 | 3/1983 | Hanifl . |
| 4,409,990 | 10/1983 | Mileikowsky . |
| 4,452,358 | 6/1984 | Simpson . |
| 4,453,648 | 6/1984 | Harris et al. . |
| 4,454,944 | 6/1984 | Shillington et al. . |
| 4,466,538 | 8/1984 | Gianni . |
| 4,485,918 | 12/1984 | Mayer . |
| 4,488,643 | 12/1984 | Pepper . |
| 4,490,142 | 12/1984 | Silvern . |
| 4,494,652 | 1/1985 | Nelson et al. . |
| 4,520,926 | 6/1985 | Nelson . |
| 4,552,280 | 11/1985 | Owen et al. . |
| 4,576,281 | 3/1986 | Kirksey . |
| 4,580,688 | 4/1986 | Harris et al. . |
| 4,585,138 | 4/1986 | Jonkers . |
| 4,596,562 | 6/1986 | Vernon . |
| 4,600,112 | 7/1986 | Shillington et al. . |
| 4,610,667 | 9/1986 | Pedicano et al. . |
| 4,667,821 | 5/1987 | Shillington . |
| 4,731,059 | 3/1988 | Wanderer et al. . |
| 4,738,362 | 4/1988 | Burns et al. . |
| 4,740,204 | 4/1988 | Masters et al. . |
| 4,740,205 | 4/1988 | Seltzer et al. . |
| 4,788,986 | 12/1988 | Harris . |
| 4,798,587 | 1/1989 | Willoughby . |
| 4,801,013 | 1/1989 | Bruno . |
| 4,802,579 | 2/1989 | Hall et al. . |
| 4,807,344 | 2/1989 | Kelson et al. . |
| 4,822,343 | 4/1989 | Beiser . |
| 4,828,107 | 5/1989 | Spencer . |
| 4,840,619 | 6/1989 | Hughes . |
| 4,841,985 | 6/1989 | Wanamaker . |
| 4,844,245 | 7/1989 | Bennett . |
| 4,867,309 | 9/1989 | Germain . |
| 4,869,366 | 9/1989 | Bruno . |
| 4,874,103 | 10/1989 | Quisenberry et al. . |
| 4,892,525 | 1/1990 | Hermann, Jr. et al. . |
| 4,904,244 | 2/1990 | Harsh et al. . |
| 4,907,600 | 3/1990 | Spencer . |
| 4,917,243 | 4/1990 | Abrams et al. . |
| 4,922,597 | 5/1990 | Ikeda et al. . |
| 4,942,881 | 7/1990 | Al-Sioufi et al. . |
| 4,974,603 | 12/1990 | Jacobs . |
| 4,984,580 | 1/1991 | Wanamaker . |
| 4,986,811 | 1/1991 | Thead et al. . |
| 4,989,307 | 2/1991 | Sharpe et al. . |
| 4,993,426 | 2/1991 | Spencer . |
| 4,995,871 | 2/1991 | Sasaki et al. . |
| 5,021,049 | 6/1991 | Howard . |
| 5,046,613 | 9/1991 | Baudry et al. . |
| 5,062,837 | 11/1991 | Al-Sioufi et al. . |
| 5,067,949 | 11/1991 | Freundlich et al. . |
| 5,069,225 | 12/1991 | Okamura . |
| 5,086,922 | 2/1992 | Sagstetter et al. . |
| 5,092,462 | 3/1992 | Sagstetter et al. . |
| 5,097,950 | 3/1992 | Weiss et al. . |
| 5,098,404 | 3/1992 | Collins . |
| 5,117,837 | 6/1992 | Wanamaker et al. . |
| 5,120,311 | 6/1992 | Sagstetter et al. . |
| 5,127,522 | 7/1992 | Ranford . |
| 5,143,083 | 9/1992 | Al-Sioufi et al. . |
| 5,187,850 | 2/1993 | McCammon et al. . |
| 5,188,598 | 2/1993 | Thead et al. . |
| 5,219,333 | 6/1993 | Sagstetter et al. . |
| 5,246,423 | 9/1993 | Farkas . |
| 5,273,161 | * 12/1993 | Sagstetter .............................. 206/366 |
| 5,299,687 | 4/1994 | Hanifl . |
| 5,312,346 | 5/1994 | Han . |
| 5,322,164 | 6/1994 | Richardson et al. . |
| 5,356,383 | 10/1994 | Daly et al. . |
| 5,409,112 | 4/1995 | Sagstetter . |
| 5,409,113 | 4/1995 | Richardson et al. . |
| 5,474,181 | * 12/1995 | Shillington et al. ................. 206/366 |
| 5,476,106 | 12/1995 | Gartz . |
| 5,540,662 | 7/1996 | Nicholson . |

* cited by examiner

SYSTEM FOR DISPOSAL OF CONTAMINATED MEDICAL PRODUCTS

This application is a continuation of Ser. No. 08/670,270 filed on Jun. 21, 1996 now abandoned.

BACKGROUND OF THE INVENTION

1. Field of the Invention

The present invention relates to safely disposing of medical waste, particularly needles and the like, in a manner which minimizes the danger of transmission of infectious diseases. More specifically, this invention is directed to a disposal system and, especially, to such a system which comprises a receptacle for contaminated medical products of the type which comprise a hub, the products also typically including a needle, the system additionally comprising a holder which cooperates with the products so as to cause a product mounted to the holder to be automatically detached from the holder and deposited within the receptacle. Accordingly, the general objects of the present invention are to provide novel and improved methods and apparatus of such character.

2. Description of the Related Art

A wide variety of blood collection/fluid injection devices are used by the health care industry. These devices include a hollow bored member, hereinafter a "hub", for transferring fluid materials via a cannula, hyopodermic needle or via the hub itself thereby providing a connective conduit for the fluid path. The hub may be tapered, and/or may be externally threaded or may have some other external configuration to faciliate and provide attachment means. These hub based devices include hypodermic syringes and blood collection/fluid injection systems. While hypodermic syringes normally have a fluid chamber integrally formed with the needle holder, blood collection/fluid injection systems typically include a needle holder having a hub detachably mounted thereon so that a needle is disposed at one end of the holder and a fluid collection tube may be inserted in the other end of the holder.

For both economic and safety reasons a wide variety of venipuncture devices has been developed. Economic factors have favored designs having associated holders which allow hub removal whereby reuse of the holder is permitted. Safety concerns, however, have pointed away from the use of such devices because the hub removal procedure creates an increased risk of inadvertent contact between the health care worker and a patient's bodily fluids and, particularly, an accidental needle stick. In recent years, increased concern about the transmission of infectious diseases, such as HIV and HBV, has renewed interest in developing safer methods and apparatus for disposing of infectious medical waste. Most of the development efforts to date have been directed toward simplifying the process of removing a hub from a holder while simultaneously minimizing the health care worker's contact with the "sharp" which is affixed to or integral with the hub. In particular, these efforts have been directed toward improving both hub retaining mechanisms and complementary hub removing means which are integrated with sharps disposal receptacles.

Sharps receptacles designed for removing a standard externally threaded hub from a holder typically possess a hollow base portion for receiving the detached devices, and a cover having various shaped slots, known in the art as unwinder apertures or unwinder slots, for engaging a hub during needle removal. To dispose of a previously used hub with attached needle using a conventional sharps receptacle, a health care worker must carefully position the hub in the appropriate slot and then grip and rotate the holder to unthread the hub so that it and the attached needle may fall through the slot into the underlying body of the receptacle. When using these devices, it is often difficult to tell when the hub has been fully unwound from the holder. Since the health care worker may be simultaneously performing other tasks, there exists a serious danger that a hub may "hang-up" and the associated needle inadvertently contact an unsuspecting health care worker. A further deficiency of prior art devices of the type being discussed stems from the lack of any product misuse prevention features. For example, the use of hubs which only appear to be compatible with a given unwinder slot may cause a malfunction. Where the hub is attached to a double-ended needle, i.e., a cannula, a further danger arises after the hub is disengaged from a holder because the hub may remain lodged in the slot, causing exposure of the upstanding posterior end of the cannula. In such a case, the user must physically handle the hub to remove it from the slot and permit the cannula hub assembly to drop into the sharps receptacle.

Aside from hub-engaging unwinder slots, other medical "sharps" removal schemes have been developed. These include the use of sharps receptacles having movable jaws which engage the standard externally threaded hub of a needle assembly. Such devices allow a user to unthread the hub/needle combination from a holder by (1) inserting the hub into a sharps box having such jaws; (2) operating the jaw mechanism to lock the hub; (3) rotating the holder to unthread the hub from the holder; and (4) releasing the locking mechanism to allow the now threadably removed hub and needle combination to fall into the sharps container base. While some sharps disposal containers of this nature can effectively remove threaded hubs, with associated needles or cannulas from holders, they are typically complex and costly devices, the complexity having a deleterious effect on reliability. Additionally, such sharps receptacles still require the health care worker to follow a relatively lengthy and complex manual hub-unwinding procedure. As with less complicated devices having unwinder slots, these receptacles periodically suffer from the problem of incomplete hub unwinding. Finally, safety is again compromised by the lack of any means for preventing operator misuse.

A similar style of disposal system, which has both increased safety and a simplified hub removal procedure, includes a sharps receptacle with an electric hub-unwinding mechanism. Sharps receptacles of this nature allow a health care worker to simply insert a holder having a hub/needle combination received therein into an aperture whereby the hub is unthreaded from the holder by means of an electric motor. Deficiencies associated with these mechanical sharps disposal systems include the facts that the receptacles are (1) very expensive to build and maintain; and (2) not easily transportable because they require some kind of electric power supply. Further, while incomplete hub unwinding is less of a problem with these systems, none of these power driven systems include any type of operator misuse prevention feature.

Finally, sharps disposal systems have been proposed wherein the sharps disposal container cooperates with a custom hub holder to effect needle release. Some of these proposed disposal systems are allegedly compatible with cannula assemblies having an externally threaded hub. While such a system would theoretically increase the safety of the "sharps" removal procedure, a rather complex series of steps would be required to achieve removal. Thus, increased safety is achieved at the expense of simplicity of operation. One proposed system for use with a custom holder requires that an adapter be placed on the hub, the hub of a cannula assembly for example, in order to make the cannula assembly compatible with the holder. The need for a hub adapter obviously results in a cost increase. Finally, neither the holder nor the sharps container of the proposed systems have any means to prevent a health care worker from using them with other, potentially incompatible, devices. Thus, safety is again sacrificed by the lack of operator misuse prevention features.

Co-pending U.S. Pat. App. No. 08/580,322, filed on Dec. 28, 1995, now U.S. Pat. No. 5,755,673, issued May 26, 1998 on continuation application Ser. No. 08/904,411 filed on Aug. 1, 1997, is directed to an improved holder for a fluid collection and/or injection system. That application has been assigned to the assignee of the present invention and the information disclosed therein is hereby incorporated by reference. The holder shown and described in application 08/580,322 possesses an actuation mechanism at one end of the holder. The actuation mechanism enables the mounting of the externally threaded hub of a cannula assembly on the holder and the maintaining of the attachment of the cannula assembly to the holder during use. Initially, the threaded hub will be threadably engaged by the actuation mechanism of the holder in the same manner as the hub/needle combination would be installed in any other medical device holder which accepts a threaded hub. Upon operation of an external actuator of the actuation mechanism, the hub is released from the actuation mechanism whereby the hub/needle combination will fall from the holder under the force of gravity. In one embodiment of the holder, the actuator is in the form of a push-button which is capable of being depressed by the operator's finger. Thus, this medical sharps holder configuration offers both compatibility with standard threaded hubs and a safe and simple means of removing a hub, particularly a hub which is integral with a cannula or needle, from the holder. However, while the holder of the aforementioned co-pending application represents a substantial advance in the sharps disposal field, some methods and apparatus of safely disposing of used hubs from such a holder are beyond the scope of the incorporated application. Thus, some aspects of the sharps disposal system of the present application represent improvements on the holder shown and described in the incorporated application.

SUMMARY OF THE INVENTION

It is an object of the present invention to provide a sharps disposal system which will permit simple, safe and effective disposal of hubs, and particularly hubs integrated or associated with needles and cannulas.

Another object of the invention is to provide a sharps disposal system comprising a holder for releasably engaging a hub and a cooperating sharps receptacle which is capable of permitting more precise and reliable single-handed remote disposal of a standard threaded hub or hub/needle combination.

It is yet another object of the present invention to provide such a disposal system which permits more precise and reliable detachment of a standard threaded cannula assembly, i.e., an externally threaded hub and associated cannula, from a holder by simply placing the holder into a complementary structure of a sharps disposal receptacle.

It is still another object of the present invention to provide a medical sharps disposal system which is of simple, durable construction and is economical to manufacture.

Another object of the present invention is to provide a sharps disposal receptacle having a safer means for removing a hub from a cooperating needle holder than has characterized the prior art.

Still another object of the present invention is to provide a sharps disposal receptacle having an operator misuse prevention feature.

These and other objects and advantages of the present invention are achieved in one embodiment by providing a holder with an actuation mechanism capable of detachably mounting a hub, and particularly the standard threaded hub of a needle assembly, onto the holder and a sharps disposal receptacle having a cover with an automatic release structure for engagement with and operation of the actuation mechanism of the holder.

In a preferred embodiment of the present invention, the actuation mechanism of the holder component of the sharps disposal system includes an actuator element, extending outwardly from, and slidably mounted to, the body of the holder. The actuator element is operably associated with other components of the actuation mechanism such that the actuation mechanism is normally biased to a position capable of engaging the external threads on a hub having a cannula extending therethrough for fluid transfer purposes. The actuator element includes a release structure guide channel extending through at least a portion of the actuator element which projects laterally outwardly from the holder body. This channel is oriented substantially parallel to the axis of the holder body and possesses a sloped face. Upon operation of the actuator element, the hub of an engaged needle assembly becomes detached from the actuation mechanism and the hub and needle are free to fall as a unit from the holder under the force of gravity. The holder includes an end cap for maintaining the actuation mechanism in the holder. The end cap includes a guide channel-access recess aligned with an actuator element channel for permitting access to the sloped face of the guide channel.

A system in accordance with the present invention also includes a sharps disposal receptacle. In a first embodiment, this receptacle has a hollow base (or, alternatively, body) for receiving medical waste therein and a receptacle cover for covering the open end of the base. The cover includes an automatic release (also referred to as "auto-release") structure which is designed to cooperate with the holder such that a standard threaded hub will be detached from the holder upon the establishment of operative engagement between the automatic release structure and the actuator element of the holder. The automatic release structure includes, in the embodiment being described, an aperture located between, and at a spaced distance from, a pair of holder guide walls which extend from the cover of the sharps receptacle. The guide walls guide one end of the holder between the inner surfaces of the guidewalls such that the hub of a hub/needle combination received within the holder may pass through the aperture. A shoulder on one of the guide walls is sized and shaped to pass through the channel-access (or, alternatively shoulder-access) recess of the end cap and mate with the sloped face of the channel in the actuator element of the holder. Thus, as the holder moves downwardly, the shoulder imparts linear motion to the actuator element. This, in turn, imparts motion to the hub engaging components of the actuator mechanism, and the now detached hub and needle combination passes through the aperture and into the base of the sharps receptacle.

In accordance with a second embodiment of a sharps receptacle for use in practice of the invention, the automatic release structure includes an aperture located between, and at a spaced distance from, a plurality of uniformly spaced elevated protrusions. Any pair of these protrusions may function as the guide structure for the holder while a third protrusion functions as the release actuation structure. As a holder is contacted by the guide structure, and then moved downwardly, the actuation protrusion imparts linear motion to the actuator element of the holder. This, in turn, imparts motion to the hub-engaging components of the actuator mechanism, and the now detached hub, typically with a needle affixed thereto, passes through the aperture and into the base of the sharps receptacle.

A sharps receptacle in accordance with the present invention preferably also includes novel means for manually unwinding a hub from a holder. Such a sharps receptacle also has an oversized aperture for inserting various other types of medical waste into the base of the sharps receptacle. Finally, a sharps receptacle in accordance with the invention is additionally provided with plural lids for selectively opening and closing the various apertures in the cover of the receptacle.

The present invention offers enhanced safety characteristics relative to prior art devices and methods. This increase in safety is partially due to the simple operation of the auto-release feature of the sharps disposal system. To dispose of a used hub/needle or hub/cannula combination with the present invention, the health care worker simply orients a holder with an engaged hub above the autorelease structure of the sharps disposal receptacle and then places the holder into the auto-release structure. As the actuator channel of the holder actuator element engages the shoulder on one of the guide walls or one of the protrusions, the hub previously mounted in the holder becomes detached and drops into the base of the sharps receptacle. in some embodiments of the present invention, overall safety is further enhanced by the inclusion of user misuse prevention features. For example, misuse prevention is achieved in the present invention by forming the sharps receptacle with an automatic release structure which unambiguously mates with and exclusively operates the actuation mechanism of a companion holder. Similarly, the configuration of the holder prevents actuation of the actuation mechanism by any other sharps receptacle. Therefore, system safety is enhanced by minimizing the possibility that a health care worker will cause incomplete needle release by attempting to use -experimental combinations of system components.

Some embodiments of the present invention also include a sharps receptacle with a novel unwinder aperture which is incapable of inadvertently being used to tighten the hub of a hub/needle combination to a holder.

Another significant advantage offered by the present invention relative to various prior art methods and devices for disposing of standard threaded medical sharps, is an optimal combination of reduced cost and efficient usage.

BRIEF DESCRIPTION OF THE DRAWINGS

The present invention will now be described with reference to the accompanying drawings wherein like numerals represent like structures and in which.

DETAILED DESCRIPTION OF THE DISCLOSED EMBODIMENTS

Figure 1:
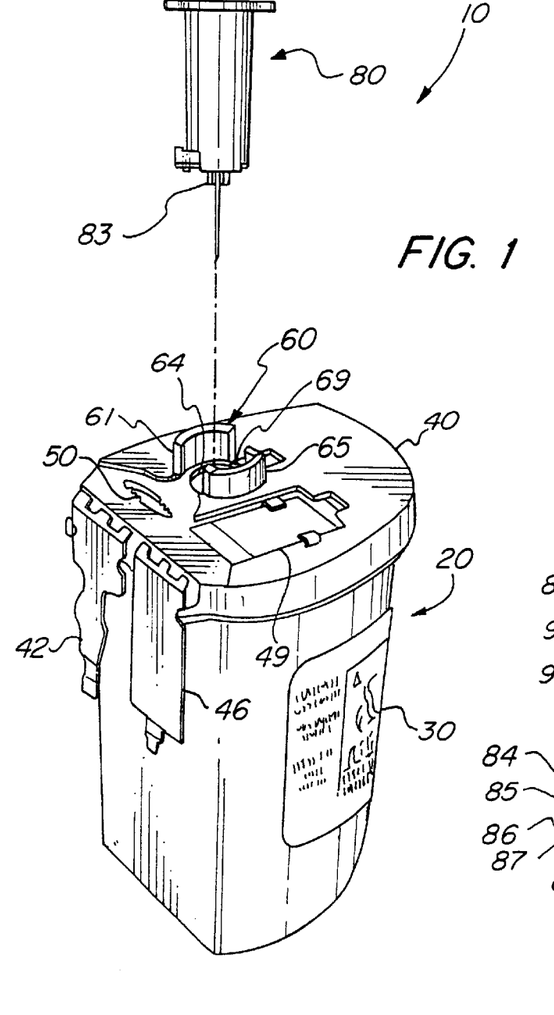
FIG. 1 is a perspective view of a first embodiment of a sharps disposal system in accordance with a first embodiment of the present invention.
Figures 3, 4:
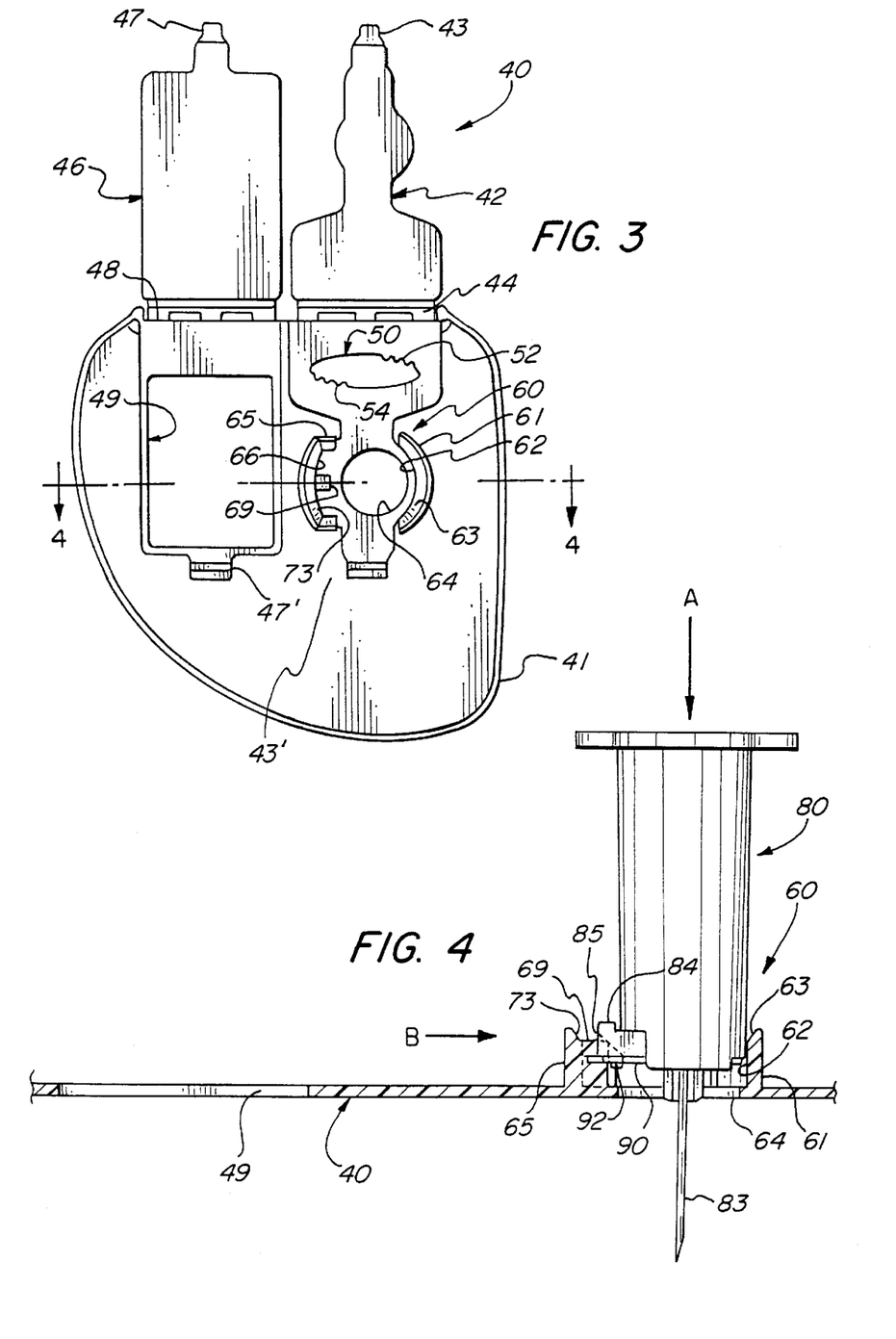
FIG. 3 a top plan view of the sharps disposal receptacle of FIG. 1.
FIG. 4 is a partial cross-sectional view of the top of the sharps receptacle of FIG. 3 taken along line 4—4 of FIG. 3, FIG. 4 also schematically showing the holder of FIGS. 1 and 2.

Referring to the drawings, and particularly FIG. 1, a sharps disposal system, indicated generally at 10, includes a holder 80 and a sharps disposal receptacle 20. Although not a part of system 10, an externally threaded hub 83, having a needle affixed thereto, is shown detachably mounted to needle holder 80. Sharps receptacle 20 includes a generally hollow base 30 for receiving contaminated sharps. Base 30 is a unitary structure and is provided with a cover 40. Each of base 30 and cover 40 have been individually injection molded to an appropriate thickness using a puncture resistant and leak-proof material such as polypropylene. Base 30, in a preferred embodiment, has a medical waste receiving capacity of approximately one quart. Referring jointly to FIGS. 1, 3 and 4, cover 40 includes a first lid 42, a second lid 46, an unwinder aperture 50, an oversized aperture 49, and an auto-release structure which has been indicated generally at 60. Auto-release structure 60, in accordance with a first embodiment, includes first and second guide walls, 61 and 65 respectively, extending substantially perpendicularly from cover 40 and positioned in spaced relation to a needle passage aperture 64. As may best be seen from FIGS. 3 and 4, a generally rectangular shoulder 69 extends from one side of second guide wall 65. As illustrated in FIG. 1, holder 80 has been positioned relative to auto-release structure 60 such that, upon downward movement of holder 80, shoulder 69 and first and second guide walls 61, 65 will orient needle holder 80 so that the needle affixed to hub 83 will extend through aperture 64.

Figure 6:
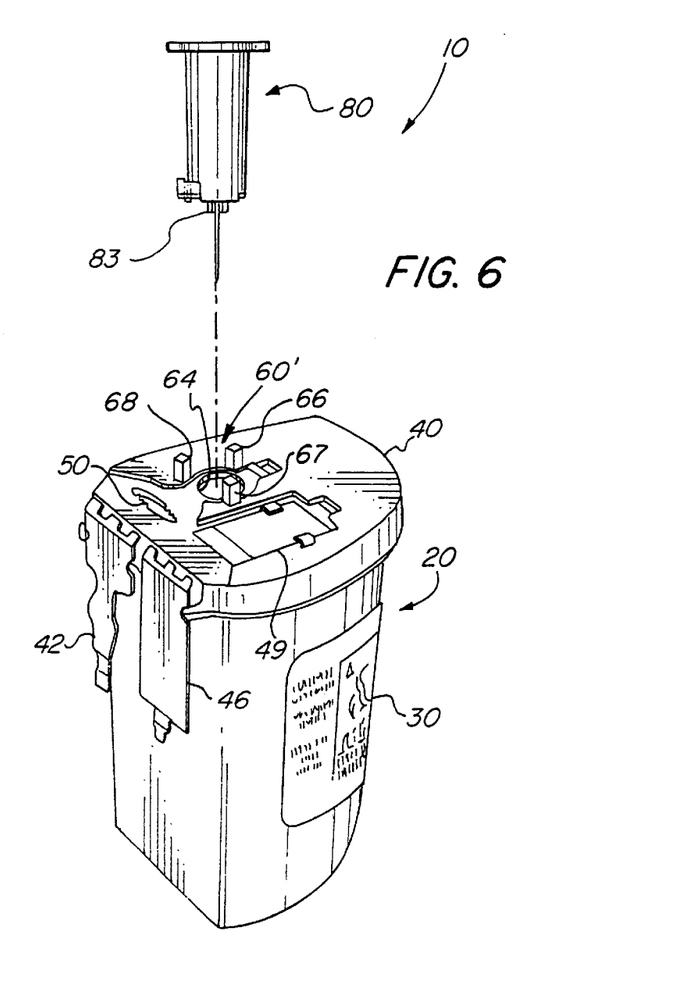
FIG. 6 is a view similar to FIG. 1 which depicts a sharps disposal receptacle in accordance with a second embodiment of the invention.
Figure 7:
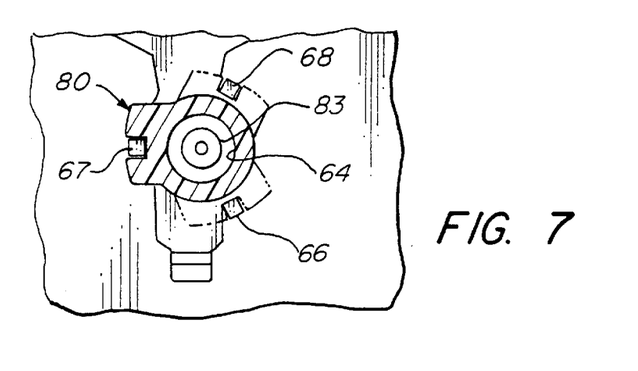
FIG. 7 is a partial top plan view of the receptacle of FIG. 6, FIG. 7 showing details of the auto-release structure of the receptacle.

The auto-release structure in accordance with a second embodiment may be seen from FIGS. 6 and 7. This alternative auto-release structure, indicated generally at 60', includes three protruding posts 66, 67, 68 extending substantially perpendicularly from cover 40 and positioned in a circular, evenly spaced relation to needle passage aperture 64. The height of posts 66–68 is sufficient to establish an operative relationship with the holder activation mechanism. As illustrated in FIG. 6, holder 80 has been positioned relative to auto-release structure 60' such that, upon downward movement of holder 80, two posts 66, 67 will guide and orient the holder 80 so that the needle affixed to hub 83 will extend through aperture 64. The third post 68 will engage the needle release mechanism. Three possible orientations of holder 80 onto posts 66, 67, 68 will result in actuation of the release mechanism.

Figure 2:
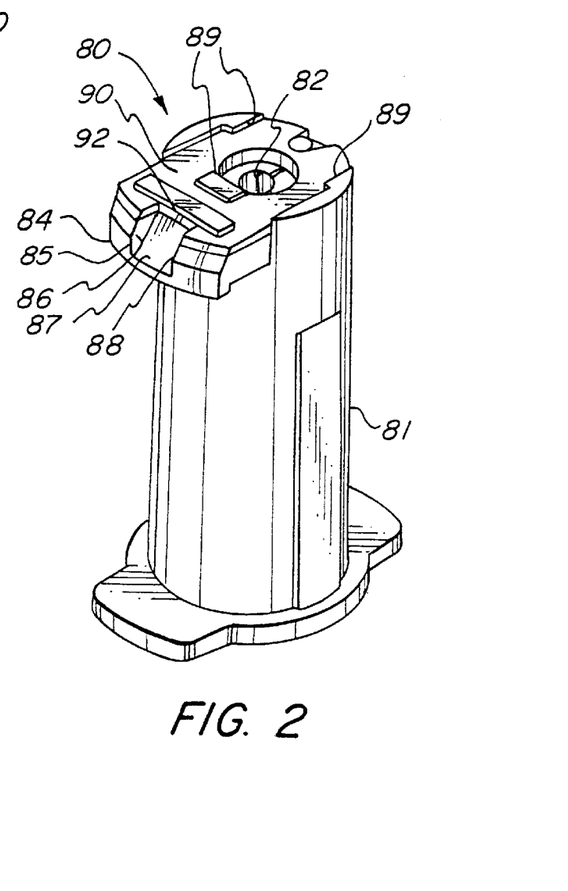
FIG. 2 is a perspective view of the needle holder of the embodiment of FIG. 1.

An enlarged perspective view of holder 80 is shown in FIG. 2. As illustrated therein, holder 80 consists of a body 81, an actuation mechanism 82 and an end cap 90. End cap 90 is used to retain actuation mechanism 82 in holder 80 and is itself retained in holder 80 by flanges 89. End cap 90 includes an aperture which permits hub/needle combinations to be inserted into actuation mechanism 82. Additionally, end cap 90 includes a recess 92 at one end thereof. As shown, recess 92 is generally rectangular.

Actuation mechanism 82 includes an actuator 84 which is normally biased outwardly with respect to body 81, to the position shown in FIG. 2. In this position, a guide channel 85 in the actuation mechanism is, at its deepest point, substantially aligned with the base of recess 92 in end cap 90. Channel 85 has a constantly and smoothly decreased depth and, in part, is defined by a pair of facing side walls 86 and 88, which are preferably in alignment with the side walls of recess 92. Channel 85 also includes a sloped face, i.e., a cam surface, 87 which slopes away from the axis of holder body 81. As shown in FIG. 2, both end cap 90 and actuator 84 possess a bevelled outer surface at one end thereof which assists with appropriate alignment of the needle holder during venipuncture. While end cap 90 is preferably fixedly attached to holder 80, actuator 84 is slidably mounted to holder 80 for reciprocal movement in a direction generally perpendicular to the axis of body 81. The various other components of actuation mechanism 82, and their interaction with a hub 83 (see FIG. 1), are described in greater detail in above-referenced co-pending U.S. Pat. application No. 08/580,322.

As shown in FIG. 2, when actuator 84 is in the outward position, actuation mechanism 82 is biased to a hub engaging position. In this position, a standard threaded hub, for example a hub integrate with a needle to form a hub/needle combination, can be threaded into actuation mechanism 82 and firmly supported by holder 80. Upon movement of actuator 84 toward the axis of body 81, hub 83 detaches from actuation mechanism 82 such that, if holder 80 were inverted from the FIG. 2 orientation, hub 83 and the associated needle would be free to fall from holder 80 under the influence of gravity.

Also as shown in FIG. 2, channel 85 preferably extends through a relatively small central region of actuator 84 so that actuator 84 can be, optionally, operated by using a finger. The extension of end cap 90 outwardly in substantial alignment with actuator 84 minimizes the possibility of inadvertent operation of actuator 84 whereby the rigid support for hub 83 would be disrupted at an inopportune moment. Similarly, end cap 90 cooperates with actuator 84 to ensure, as will be discussed in more detail below, that hubs are automatically detached from holder 80 only by the action of the complementary auto-release structure of sharps receptacle 20 (FIG. 1).

Referring to FIG. 3, a top plan view of sharps receptacle 20 of system 10 is shown. Cover 40 of receptacle 20 includes a generally cat's-eye shaped unwinder aperture 50. Undulating portions 52 and 54, of generally sinusoidal shape, are included in the opposite elongated sides of the perimeter of aperture 50 as shown. The central region of aperture 50 is sized and shaped to comfortably receive a hub of a needle/hub combination, such as hub 83. As a result of movement of the hub either to the left or to the right from the insertion position, i.e., movement away from the central region of aperture 50, the undulating portions 52 or 54 will engage the hub and impede counter-clockwise rotation thereof. This engagement allows an operator to manually unthread hub 83 from holder 80. Thus, using unwinder aperture 50, a health care worker has the option of manually unscrewing hub 83 from holder 80 in the conventional manner. The positioning undulating portions 52 and 54, as shown in FIG. 3 provides the advantage that undulating portions 52 and 54 will only mechanically engage a hub as the hub is unwound, i.e., rotated in the counter-clockwise direction, from a holder. Thus, a health care worker cannot inadvertently overtighten a hub to a holder when attempting to unwind the hub from the holder.

Figure 5A:
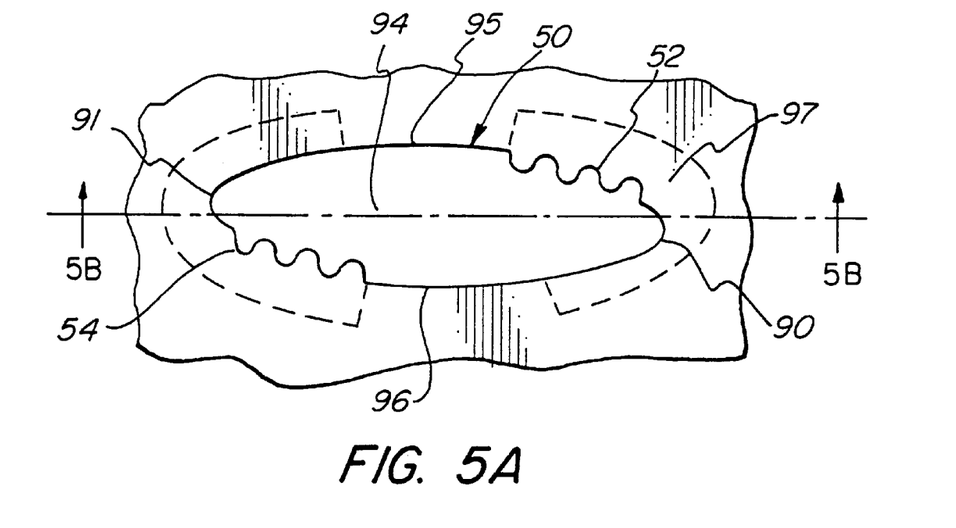
FIGS. 5A and 5B are respectively enlarged partial top plan and cross-sectional side elevation views of the top of the receptacle which show details of the unwinder aperture.
Figure 5B:
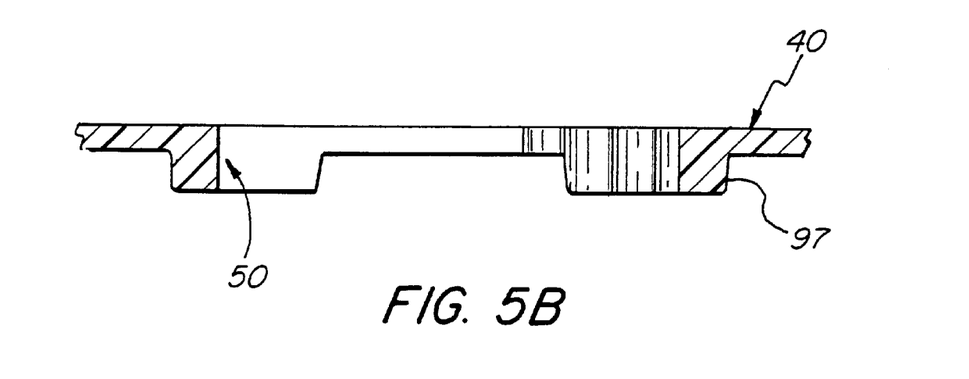

FIGS. 5A and 5B show the unwinder aperture 50 in greater detail. The opposite, narrow ends 90 and 91 of aperture 50 interconnect, and thus define the ends of a pair of opposed aperture sides 95, 96. Sides 95 and 96 are in the form of substantially equal radii arcs. The central portions of arcuate sides 95 and 96 are spaced sufficiently to permit the free passage of hubs, such as hub 83, therethrough. The undulating portions 52 and 54 are located between the central or free-drop portions of the aperture defined by arcuate sides 95 and 96 and respective ones of the ends 90 and 91. Each undulating portion is located opposite from a smoothly curved wall. As may clearly be seen in FIG. 5B, cover 40 is provided with regions of increased thickness which extend at least part way about the periphery of aperture 50, these enlarged width portions increasing the strength of the cover 40.

As shown in FIG. 3, cover 40 also includes oversized aperture 49 for receiving assorted infectious medical waste such as hypodermic syringes, winged infusion sets and catheters of appropriate size. While aperture 49 is shown as being generally rectangular, it can, of course, also be any one of many other shapes as long as aperture 49 is sufficiently large to easily receive the aforementioned medical products. Aperture 49 may have a notch along one side thereof to facilitate disposal of waste products and have standard Luer fittings or adapters. Once these products have passed through aperture 49, second lid 46 may be used to seal aperture 49 and prevent inadvertent spillage of infectious medical waste.

Second lid 46 is pivotably mounted to one end of cover 40 via a second hinge 48. Second lid 46 is preferably integrally formed with cover 40 and second hinge 48 is preferably sized and shaped to provide a durable, yet flexible, hinge for repeated usage. Thus, to provide access to oversized aperture 49, second lid 46 is pivoted away from aperture 49. Similarly, aperture 49 can be closed by pivoting second lid 46 toward cover 40. For allowing temporary closure, second lid 46 may have any suitable means, such as detents, which snap-fit into complementary elements on cover 40. Aperture 49 can be permanently closed by pivoting second lid 46 toward cover 40 and slipping a locktab 47 into a lock-slot 47'. This would be done, for example, once the infectious medical waste has substantially filled sharps receptacle 20.

Cover 40, as noted above, also includes auto-release structure 60 (FIG. 1) or 60'. Structure 60 preferably includes needle passage aperture 64 disposed between, and in spaced relation to, guide walls 61 and 65 and structure 60' preferably includes needle passage 64 disposed between, and in spaced relation to posts 66, 67 and 68. As can be seen from FIG. 3, which is a further showing of the receptacle of FIG. 1, first guide wall 61 is preferably generally arc-shaped and second guide wall 65 is preferably generally U-shaped. The concave portions of first and second guide walls 61 and 65 face one another and are sized and shaped to receive one end of holder 80. Needle passage aperture 64 is preferably large enough to easily pass hub 83, but small enough to prevent holder 80 from passing therethrough. First guide wall 61 has a concave inner surface 62 which faces inner surface 66 on second guide wall 65. Further, as clearly shown in FIG. 4, first guide wall 61 has a chamfered edge 63 which extends downwardly and inwardly from the top of guide wall 61. Similarly, second guide wall 65 has a generally U-shaped chamfered edge 73 extending downwardly and inwardly from the top of guide wall 65. First and second chamfered edges 63 and 73 function as guides to insure proper orientation of holder 80 when holder 80 is initially inserted into auto-release structure 60. Upon further downward movement of holder 80, shoulder 69, which is preferably of uniform rectangular cross-section passes through recess 92

(FIG. 2) of end cap 90 thus positioning guide wall inner surfaces 62 and 66 adjacent the outer surface of holder 80. Since shoulder 69 only extends up to the bottom chamfered edge 73, release of actuation mechanism 82 only begins at this point. Upon further downward movement of holder 80, shoulder 69 enters actuator guide channel 85. This keyed alignment between shoulder 69 and actuator guide channel 85 further ensures appropriate and exclusive operation between auto-release structure 60 and holder 80. Still further downward movement of holder 80 forces the top edge shoulder 69 to ride along sloped face 87 of actuator guide channel 85 whereby actuator 84 is cammed toward body 81 of holder 80 in a direction which is substantially perpendicular to the axis of holder body 81. This camming action may be achieved, after contact is established between shoulder 69 and face 87 of actuator guide channel 85, by imparting a rocking motion to holder 80. The holder thus does not have to be moved axially with respect to aperture 64 but, rather, needs merely to engage guide wall surface 62 to permit the hub release action to be initiated. The inward movement of actuator 84 causes actuation mechanism 82 to detach a hub 83 previously mounted to holder 80. Thus, hub/needle combination is free to fall through needle passage aperture 64 into sharps receptacle base 30 under the force of gravity.

Central needle passage aperture 64 is preferably large enough to easily pass hub 83, but small enough to prevent holder 80 from passing therethrough. In the embodiment of FIGS. 6 and 7, positioned in a circular spaced relation to needle passage aperture 64, three protruding posts 66, 67, 68 extend substantially perpendicularly from cover 40. The height of these posts is sufficient to operatively engage the holder actuation mechanism. The width of each of posts 66, 67, 68 is sufficiently narrow to pass through recess 92 of end cap 90, into actuator guide channel 85. This keyed alignment between the posts 66, 67, 68 and the channel 85 further ensures appropriate and exclusive operation between the auto-release structure 60 and holder 80. As illustrated in FIG. 7, holder 80, shown in hatching, has been positioned relative to auto-release structure 60 such that, upon downward movement of holder 80, two posts 66, 68 will guide and orient the holder 80 so that hub 83 will extend through aperture 64 while the third post 67 enters channel 85 and contacts the hub actuator 84 on its sloped cam surface 87.

Similar to second lid 46, first lid 42 is pivotably mounted to cover 40 via first hinge 44. First lid 42 can be used to selectively open and close both needle passage aperture 64 and unwinder aperture 50 by rotation about first hinge 44. For allowing temporary closure, first lid 42 may have any suitable means such as detents which snap-fit into complementary elements on cover 40. As with second lid 46, first lid 42 includes a lock-tab 43 which is sized and shaped to engage lockslot 43' to permanently seal needle passage aperture 64 and unwinder aperture 50. Lid 42 is preferably integrally formed with cover 40 and hinge 44 is sized and shaped to provide a durable, yet flexible, hinge for repeated usage.

Cover 40 is preferably permanently affixed to base 30 (FIG. 1) at a rim 41 in snap-fit fashion. Cover 40 is engaged by base 30, preferably at rim 41, with sufficient strength so that cover 40 cannot be removed from base 30 without causing substantial damage thereto. Cover 40 and base 30 are individually injection molded from a suitable plastic material. These components may, however, vary in certain respects. For example, base 30 is preferably formed of a red opaque material. By contrast, cover 40 is preferably formed of either a translucent or transparent material. This allows health care workers to monitor the amount of accumulated waste material inside sharps receptacle 20. Medical waste level monitoring may be further assisted by the presence on base 30 of a fill-line (not shown) extending around the surface of base 30. Thus, by forming cover 40 of translucent material, and by the inclusion of a fill-line on base 30, a health care worker may easily determine when sharps receptacle 20 is sufficiently full. When sharps receptacle 20 has become sufficiently full with waste material, a health care worker may permanently seal sharps receptacle 20 by closing lids 42 and 46 and slipping lock-tabs 43 and 47 into lock-slots 43' and 47' respectively. Thereafter, the sealed sharps receptacle 20 can be discarded in an appropriate manner as a single unit. It should be noted that, since guide walls 61 and 65 preferably extend upwardly from cover 40, more medical waste may be received within base 30 relative to prior art sharps receptacles having release mechanisms located within the interior of the sharps receptacle. Thus, the present invention more efficiently utilizes the space available for receiving medical waste.

Referring again to FIG. 4, the cooperation between needle holder 80 and auto-release structure 60 in the embodiment of FIGS. 1 and 3 will be described in still greater detail. In FIG. 4, cover 40 is depicted in partial cross section taken along line 4-4 of FIG. 3. Holder 80, by contrast, is shown in side elevation view. As shown in FIG. 4, holder 80 has been partially placed into auto-release structure 60 in the direction of arrow A. Channel 85 and shoulder-access recess 92, shown in phantom, are in engagement with shoulder 69, such that actuator 84 has experienced some minimal movement in the direction of arrow B. In this position, hub 83 has not yet become detached from actuation mechanism 82. Upon further movement of holder 80 in the direction of arrow A, end cap 90 will come into abutting relationship with cover 40 at the bottom of first and second guide walls 61 and 65. At this time, actuator 84 will have moved in the direction of arrow B, i.e., channel 85 will have moved to the position where shoulder 69 has reached the end of channel 85. In this position, hub 83 is detached from actuation mechanism 82 and is free to fall from holder 80 into base 30 of sharps receptacle 20 (FIG. 1) in the direction of arrow A. Upon removal of holder 80 from auto-release structure 60 in a direction opposite of that of arrow A, holder 80 resumes its normal configuration, as shown in FIG. 2, and is ready for reuse. The operation of the embodiment of FIGS. 6 and 7 is, of course, substantially identical to the above-described operation of the FIGS. 1 and 3 embodiment.

It will be readily appreciated by one of ordinary skill that the present invention incorporates a number of safety features not present in the prior art. First and foremost is that holder 80 and both disclosed embodiments of auto-release structure 60 are specifically designed for use with one another. For example, end cap 90 of holder 80 effectively precludes movement of actuator 84 when holder 80 is inserted into non-compatible disposal containers, such as containers of the type having a generally conical opening. Thus, health care workers are effectively prevented from attempting to use holder 80 with incompatible sharps containers. Similarly, the arrangement of first and second guide walls 61 and 65, or the array of posts 66–68, and rectangular shoulder 69 effectively prevents auto-release structure 60 from being used with other needle holders. Thus, while holder 80 can be hand-operated, the exclusive compatibility between holder 80 and auto-release structure 60 ensures that experimental combinations of components are precluded.

The cooperation between holder 80 and auto-release structures 60 significantly improves the reliability of the hub detachment operation. For example, the sizing, spacing and arrangement of first and second guide walls 61 and 65 or posts 66–68 and rectangular shoulder 69 ensures that actuator 84 is sufficiently, but not overly, depressed each time holder 80 is fully placed into auto-release structure 60. This ensures proper detachment of hub 83 from holder 80 while extending the life of holder 80 by preventing over-stressing of actuation mechanism 82. Similarly, the sizing and location of needle passage aperture 64 ensures that holder 80 will never pass into, or become lodged in, sharps receptacle 20. This arrangement also ensures that a health care worker can easily recognize when the needle detaching procedure has been completed. Similarly, the first and second chamfered edges 63 and 73 in the embodiment of FIGS. 1 and 3 help ensure proper alignment between holder 80 and first and second guide walls 61 and 65. This feature further enhances the speed and accuracy of the hub detachment operation. Thus, successful hub detachment is virtually ensured using the methods and apparatus of the present invention.

Having described two preferred embodiments of the present invention with reference to the accompanying drawings, it will be appreciated that various changes and modifications can be effected therein by one of ordinary skill in the art without departing from the spirit and scope of the invention as defined in the appended claims.

What is claimed is:

1. A sharps disposal system for automatic detachment of the hub of a medical device from a holder comprising:
    a holder, said holder including movable actuator means for detachably mounting a hub to said holder; and
    a sharps receptacle having a generally hollow base with an open end and a generally rigid cover for closing said open end of said base, said cover having a hub passage aperture sized and shaped to permit passage of a hub into the interior of the receptacle, said cover also having a release structure which alighns said holder with said aperture and which engages said actuator means of said holder, said release structure operating said actuator means to cause detachment of a mounted hub from said holder, said release structure extending upwardly from said cover and being in spaced relationship to said aperture in said cover such that a hub detached from said holder by operation of said release structure will pass into said sharps receptacle as a result of placement of said holder into engagement with said release structure.

2. A sharps disposal system as recited in claim 1, wherein said actuator means comprises a linearly movable actuation mechanism, wherein said aperture in said cover is smaller than said holder and larger than the largest portion of the hub, and wherein:
    said release structure comprises first and second guide walls for aligning said holder with said aperture, said guide walls extending substantially perpendicularly from said cover; and
    said release structure further comprises an actuator means engaging projection extending from said cover, said projection engaging said actuation mechanism of said holder to thereby cause detachment of a hub from said holder.

3. A sharps disposal system as recited in claim 2 wherein said projection is integral with one of said guide walls.

4. A sharps disposal system as recited in claim 2 wherein said first and second guide walls and said projection comprise separate, spatially displaced members.

5. A sharps disposal system as recited in claim 2, wherein said cover further comprises:

a hub unwinder aperture extending through said cover, said unwinder aperture being sized and configured to engage and impede rotation relative to a holder of a threaded hub;
an oversized aperture extending through said cover for inserting medical waste into said sharps receptacle;
a first lid pivotably mounted to said cover for selectively opening and closing said hub passage aperture and said unwinder aperture simultaneously; and
a second lid pivotably mounted to said cover for selectively opening and closing said oversized aperture.

6. A sharps disposal system as recited in claim 2, wherein each of said first and second guide walls includes a top, an outer surface, an inner surface which faces the inner surface of the other of said guide walls and a chamfered edge at said top, said chamfered edge extending downwardly from said outer surface toward said inner surface to assist placement of said holder between said first and second guide walls.

7. A sharps disposal system as recited in claim 2, wherein said holder includes an end cap having a recess, through which said projection can pass, wherein said actuation mechanism includes an actuator element slidably mounted to said holder, said actuator element having a camming surface positioned to be contacted by a projection which passes through said recess, and wherein said projection is sized and shaped to pass through said recess whereby said projection will engage said camming surface as said holder is placed between said first and second guide walls.

8. A sharps disposal system for automatic detachment of a cannula assembly from a holder, said cannula assembly including a hub and a cannula extending through the hub and affixed thereto, said system comprising:
    holder means for releasably holding a cannula assembly through cooperation with the hub thereof; and
    a sharps receptacle having a hollow base and a cover on said base, said cover having a cannula assembly passage aperture and a release structure for aligning said holder with said aperture and for engaging said holder means such that the cannula assembly detaches from said holder means and enters into said sharps receptacle via said aperture as said holder means is placed into said release structure;
    wherein said release structure extends upwardly from said cover and is in spaced relationship to said aperture in said cover.

9. A sharps disposal system as recited in claim 8, wherein said holder means includes means for detachably mounting the cannula assembly hub to said holder means, wherein said aperture is provided in said cover, said aperture being smaller than said holder means and larger than the cannula assembly hub and wherein said release structure further comprises:
    first and second guide walls for contacting said holder means to align a cannula assembly mounted thereon with said aperture, said guide walls extending substantially perpendicularly from said cover; and
    a projection extending from said cover, said projection being configured and positioned to engage said means for detachably mounting a cannula assembly hub to said holder means, cooperation between said projection and mounting means causing detachment of the cannula assembly hub from said holder means in response to placement of said holder means between said guide walls whereby the cannula assembly may fall into said base solely under the influence of gravity.

10. A sharps disposal system as recited in claim 9, wherein said projection is integral with one of said guide walls.

11. A sharps disposal system as recited in claim 9, wherein said guide walls and said projection are equidistant from the center of said aperture and are uniformly spaced about said aperture, said guide walls and projection also being similarly configured, whereby each can perform either a guiding or detachment causing function.

12. A sharps disposal system as recited in claim 8, wherein said cover further comprises:
- a needle unwinder aperture extending through said cover, said unwinder aperture being defined by first and second spaced-apart sides terminating in a pair of opposite ends, the first and second sides each having respective undulate portions at a different one of the opposite ends, each undulate portion facing a smooth portion of the other one of the sides, said unwinder aperture further being sized and shaped to engage a cannula assembly hub whereby the facing undulate and smooth portions cooperate to prevent rotation of such cannula assembly hub in a first, tightening, direction, but permit rotation thereof in a loosening direction opposite to the first direction.

13. A sharps disposal system as recited in claim 9, wherein each of said first and second guide walls includes a top, an outer surface, an inner surface which faces the inner surface of the other of said guide walls and a chamfered edge at said top, said chamfered edge extending downwardly and inwardly from said top to said inner surface to guide said holder between said first and second guide walls.

14. A sharps disposal system as recited in claim 9, wherein said holder includes an end cap having a recess with a size and shape complementary to said projection, wherein said means for detachably mounting the cannula assembly includes an actuator element slidably mounted to said holder, said actuator element having a channel which is in part defined by an inclined cam surface, said channel being sized and positioned so as to be entered by said projection after passage thereof through said recess, and wherein said projection is shaped to operatively engage said cam surface.

15. A sharps disposal system for automatic detachment of a needle assembly from a holder, the needle assembly including an elongated member affixed to said hub, said system comprising:
- a needle holder, said needle holder having a hollow body with an end wall at a closed first end thereof, said end wall having an aperture therethrough, said hollow body also having an open second end disposed opposite to said first end for receiving a fluid container within said hollow body;
- housing means abutting said first end of said hollow body for maintaining at least a portion of an actuation mechanism within said holder, said housing means including means defining an aperture therethrough which is generally coaxial with said aperture of said needle holder end wall; and
- an actuation mechanism for releasably mounting a threaded needle assembly hub to said holder with one end of the needle extending forwardly of said actuation mechanism for venipuncture and the other end extending rearwardly into said hollow body for cooperation with a fluid container received in said body, said actuation mechanism including:
  first and second threaded halves mounted within said housing means for removably mounting the needle assembly hub upon threading of the hub into said actuation mechanism, at least one of said first and second threaded halves being movable between a hub-mounting position, and a retracted position;
  means for pivotably mounting at least one of said first and second threaded halves within said housing means; and
  actuation means slidably mounted to said housing means for movement between an initial position wherein at least one of said first and second threaded halves is urged into said cannula-mounting position, and a secondary position wherein at least one of said first and second threaded halves is urged into said retracted position; and
- a sharps receptacle having a base and a cover on said base, said cover comprises a needle passage aperture and a release structure for aligning said holder with said aperture and for operatively engaging said actuation means such that the needle assembly detaches from said actuation mechanism and enters into said sharps receptacle as a result of placement of said holder into said release structure;
- and wherein said release structure extends upwardly from said cover and is in spaced relationship to said needle passage aperture.

16. A sharps disposal system as recited in claim 15, wherein said needle passage aperture is smaller than said holder and larger than the largest portion of the needle assembly and wherein:
- said release structure comprises first and second guide walls for aligning said holder with said needle passage aperture, said guide walls extending substantially perpendicularly from said cover; and
- said release structure further comprises a projection for engaging said actuation mechanism of said holder to detach the needle assembly from said holder into said sharps receptacle as said holder is placed between said first and second guide walls, said projection extending upwardly from said cover.

17. A sharps disposal system as recited in claim 16, wherein said cover further comprises:
- an oversized aperture extending through said cover for inserting medical waste into said sharps receptacle; and
- lid means pivotably mounted to said cover for selectively opening and closing said aperture.

18. A sharps disposal system as recited in claim 16, wherein said projection is integral with one of said guide walls and wherein each of said first and second guide walls includes a top, an outer surface, an inner surface which faces the inner surface of the other of said guide walls and a chamfered edge at said top, said chamfered edge extending downwardly and inwardly from said top to said inner surface to assist placement of said holder between said first and second guide walls.

19. A sharps disposal system as recited in claim 15 wherein said at least one of said first and second threaded halves is pivotable between the hub-mounting position and the retracted position, and said means for movably mounting at least one of said first and second threaded halves within said housing means comprises means for pivotably mounting said at least one of said first and second threaded halves.

20. A sharps disposal system as recited in claim 16, wherein said holder includes an end cap having a recess sized and shaped to permit passage of said projection therethrough, wherein said actuation means includes an actuator element slidably mounted to said holder, said actuator element having a channel with an inclined bottom surface which is substantially aligned with said recess, and wherein said projection has a cross-section and shape complementary to said recess, said projection passing through said recess and engaging said channel bottom surface as said holder is placed between said first and second guide walls.

21. A sharps disposal system for automatic detachment of a cannula assembly from a holder, the cannula assembly including a hub, said system comprising:
 a needle holder, said needle holder having a hollow body with an end wall at a closed first end thereof, said end wall having an aperture therethrough, said hollow body also having an open second end opposite to said first end for receiving a fluid container within said hollow body;
 housing means affixed to and abutting said first end of said hollow body for maintaining at least a portion of an actuation mechanism within said holder, said housing means including means defining an aperture therethrough which is generally coaxial with said aperture of said holder end wall; and
 an actuation mechanism positioned in said housing means for detachably mounting a cannula assembly hub to said holder with one end of the cannula extending forwardly of said actuation mechanism for venipuncture and the other end extending rearwardly into said hollow body for engagement with a fluid container received therein, said actuation mechanism including:
 first and second mounting jaws rotatably mounted within said housing means for removably mounting the cannula assembly hub upon insertion of the hub into said actuation mechanism, said first and second mounting jaws being pivotable between a mounting position wherein said mounting jaws cooperate to define a passageway complementary in cross-sectional shape to the cross-sectional shape of the cannula assembly hub, and a retracted position wherein said mounting jaws cooperate to define an opening larger than the cannula assembly hub;
 a pivot axle for rotatably mounting said first and second mounting jaws within said housing means; and
 actuation means for urging said first and second mounting jaws between said cannula assembly-mounting and retracted positions, said actuation means being slidably mounted to said housing means for linear reciprocal movement between an initial position wherein said first and second mounting jaws are urged into said mounting position, and a second position wherein said first and second mounting jaws are urged into said retracted position;
 a sharps receptacle having a base and a cover, said cover comprising a needle passage aperture and a release structure for aligning said holder with said aperture and for engaging said actuation means such that the cannula assembly detaches from said holder in response to placement of said holder into said release structure; and
 wherein said release structure extends upwardly from said cover and is in spaced relation to said needle passage aperture.

22. A sharps disposal system as recited in claim 21, wherein said needle passage aperture is smaller than said holder and larger than the largest cross-section of the cannula assembly and wherein:
 said release structure comprises first and second guide walls for aligning said holder with said needle passage aperture, said guide walls extending substantially perpendicularly from said cover; and
 said release structure further comprises an actuation means operating projection extending from said cover, said projection being dimensioned and configured to engage said actuation means of said holder to cause detachment of the cannula assembly from said holder.

23. A sharps disposal system as recited in claim 21 wherein said first and second guide walls and said projection comprise separate, spatially displaced members.

24. A sharps disposal system as recited in claim 22, wherein said cover further comprises:
 an oversized aperture extending through said cover for inserting medical waste into said sharps receptacle; and
 lid means pivotably mounted to said cover for selectively opening and closing said oversized aperture.

25. A sharps disposal system as recited in claim 22, wherein said projection is integral with one of said guide walls and wherein each of said first and second guide walls includes a top, an outer surface, an inner surface which faces the inner surface of the other of said guide walls and a chamfered edge at said top, said chamfered edge extending downwardly from said outer surface toward said inner surface to assist placement of said holder between said first and second guide walls.

26. A sharps disposal system as recited in claim 22, wherein said holder includes an end cap having a recess sized and shaped for passage of said projection therethrough, wherein said actuation means includes an actuator element slidably mounted to said holder, said actuator element having a channel with an inclined cam surface which is substantially aligned with said recess, and wherein said projection has a substantially constant cross-section of substantially the same cross-section and size as said recess, said projection passing through said recess and engaging said channel cam surface as said holder is placed between said first and second guide walls.

27. A sharps receptacle for use with a companion needle holder of the type having a movable actuation mechanism for detachably mounting a needle assembly therein, said receptacle comprising:
 a generally hollow base with one open end;
 a generally rigid cover mounted on said open end of said base, said cover including a needle passage aperture and a release structure for aligning said needle holder with said aperture and for engaging the actuation mechanism of the needle holder, said release structure operating the actuation mechanism to cause detachment of the needle assembly from the holder into said base of said sharps receptacle as the needle holder is placed into said release structure, said release structure extending upwardly from said cover and being in spaced relation to said aperture.

28. A sharps receptacle as recited in claim 27, wherein said aperture is smaller than the needle holder and larger than the largest portion of the needle assembly; and wherein said release structure comprises:
 first and second guide walls for aligning the needle holder with said needle passage aperture, said guide walls extending substantially perpendicularly from said cover; and
 a projection extending from said guide cover, said projection engaging and imparting movement to the actuation mechanism of the holder to detach the needle assembly from the holder into said sharps receptacle as the holder is placed between said first and second guide walls.

29. A sharps disposal system as recited in claim 28 wherein said projection is integral with one of said guide walls.

30. A sharps disposal system as recited in claim 28 wherein said first and second guide walls and said projection comprise separate, spatially displaced members.

31. A sharps receptacle as recited in claim 28, wherein said cover further comprises:

a needle unwinder aperture extending through said cover for engaging a threaded needle assembly whereby the threaded needle assembly may be manually detached from a holder into said sharps receptacle, said unwinder aperture permitting rotation of an engaged assembly in only one direction;

an oversized aperture extending through said cover for inserting medical waste into said sharps receptacle;

a first lid pivotably mounted to said cover for selectively opening and closing said needle passage aperture and said unwinder aperture; and a second lid pivotably mounted to said cover for selectively opening and closing said oversized aperture.

32. A sharps receptacle as recited in claim 28, wherein each of said first and second guide walls include a top, an outer surface, an inner surface which faces the inner surface of the other of said guide walls and a chamfered edge at said top, said chamfered edge extending downwardly and inwardly from said outer surface toward said inner surface to assist placement of said holder between said guide walls.

33. A sharps receptacle as recited in claim 28, adapted for use with a needle holder having an actuation mechanism for detachably mounting a cannula therein and an end cap having a recess sized and shaped for passage of said projection therethrough, wherein said actuation means includes an actuator element slidably mounted to said holder, said actuator element having a channel with an inclined cam surface which is substantially aligned with said recess, and wherein said projection has a substantially constant cross-section of substantially the same cross-section and size as said recess, said projection passing through said recess and engaging said channel cam surface as said holder is placed between said first and second guide walls.

34. Apparatus for significantly impeding rotation in only one direction of the hub of a needle subassembly which is threadably engaged by a needle holder, said apparatus comprising:

a container for receiving detached needle subassemblies after disengagement thereof from the holder;

a top affixed to said container; and an unwinder aperture in said top, said unwinder aperture being elongated and having a centerline which extends between a pair of oppositely disposed narrow ends, said narrow ends being interconnected by a pair of oppositely disposed arcuate sides having the same radius, each of said arcuate sides including a segment which defines a plurality of teeth, said toothed segments adjoining respective narrow ends of said aperture on opposite sides of the centerline, said toothed segments extending from said respective opposite narrow aperture ends along opposite sides of said aperture for a distance which is less than half of the length of the included side.

35. The apparatus of claim 34 wherein said top further comprises:

a rim region of increased thickness which extends about at least a portion of the periphery of said aperture.

36. A sharps disposal system as recited in claim 12 wherein said cover further comprises:

an oversized aperture extending through said cover for inserting medical waste into said sharps receptacle; and lid means pivotably mounted to said cover for selectively opening and closing said apertures.

* * * * *